US006231837B1

(12) United States Patent
Stroud et al.

(10) Patent No.: US 6,231,837 B1
(45) Date of Patent: May 15, 2001

(54) SELF-TANNING DIHYDROXYACETONE FORMULATIONS HAVING IMPROVED STABILITY AND PROVIDING ENHANCED DELIVERY

(75) Inventors: Eric M. Stroud, Bayonne; John A. Scott, Succasunna, both of NJ (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/552,437

(22) Filed: Apr. 18, 2000

Related U.S. Application Data

(63) Continuation of application No. 09/092,340, filed on Jun. 5, 1998, now abandoned.
(60) Provisional application No. 60/048,903, filed on Jun. 6, 1997.

(51) Int. Cl.[7] .............................. A61K 7/42; A61K 7/44; A61K 7/00
(52) U.S. Cl. .............................. 424/59; 424/60; 424/400; 424/401
(58) Field of Search .............................. 424/59, 60, 400, 424/401

(56) References Cited

U.S. PATENT DOCUMENTS

| 3,019,165 | 1/1962 | Mansor | 167/65 |
|---|---|---|---|
| 3,281,374 | 10/1966 | Walther et al. | 252/309 |
| 3,489,690 | 1/1970 | Lechampt et al. | 252/308 |
| 3,940,477 | 2/1976 | Vanlerberghe et al. | 424/59 |
| 3,975,294 | 8/1976 | Dumoulin | 252/354 |
| 4,098,881 | 7/1978 | Majeti | 424/59 |
| 4,303,639 | 12/1981 | Vanlerberghe et al. | 424/63 |
| 4,434,154 | 2/1984 | McShane | 424/60 |
| 4,454,159 | 6/1984 | Musher | 424/358 |
| 4,466,955 | 8/1984 | Calvo et al. | 424/62 |
| 4,810,489 | 3/1989 | Murray et al. | 424/59 |
| 4,970,220 | 11/1990 | Chaussee | 514/358 |
| 5,232,688 | 8/1993 | Ziegler et al. | 424/59 |
| 5,268,166 | 12/1993 | Barnett et al. | 424/47 |
| 5,302,378 | 4/1994 | Crotty et al. | 424/59 |
| 5,437,859 | 8/1995 | Ser et al. | 424/59 |
| 5,458,872 | 10/1995 | Durand | 424/59 |
| 5,514,367 | 5/1996 | Lentini et al. | 424/59 |
| 5,514,437 | 5/1996 | Tanner et al. | 424/63 |
| 5,569,460 | 10/1996 | Kurz et al. | 424/401 |
| 5,614,178 | 3/1997 | Bloom et al. | 424/60 |
| 5,827,520 | 10/1998 | De Salvert | 424/401 |

FOREIGN PATENT DOCUMENTS

| 0 770 381 A1 | 5/1997 | (EP) . |
|---|---|---|
| 56630/94 | 3/1994 | (JP) . |
| WO 94/12146 | 6/1994 | (WO) . |

OTHER PUBLICATIONS

Collection of Well Known Prior Arts (Cosmetics and Similar Products); Japanese Patent Office, Aug. 21, 1984; with translated pp. 22 and 40.
T. Kurz, "Formulating Effective Self–Tanners with DHA," *Cosmetics & Toiletries*, vol. 109, pp. 55–56 (Nov. 1994).
J.B. Wilkinson et al., *Harry's Cosmeticology, Sixth Ed.*, Chemical Publishing Co., Inc., New York, pp. 332–335 (1973).

*Primary Examiner*—Shelley A. Dodson
(74) *Attorney, Agent, or Firm*—Robert A. Franks

(57) ABSTRACT

A composition is provided which is useful for self-tanning skin coloring and is characterized by improved stability, which comprises from about 0.5% to about 20.0% by weight, based on total weight of said composition, of a self-tanning skin coloring agent subject to chemical instability, which is preferably dihydroxyacetone; from about 2.0% to about 40.0% by weight of a polyethoxyglycol, which is preferably ethoxydiglycol; and from about 0.1% to about 15.0% by weight of a polyol comprising a polyhydric compound having at least three hydroxyl groups and at least three carbon atoms, which is preferably D-sorbitol. The self-tanning composition may further optionally contain from about 0.1% to about 8.0% by weight of a water soluble dihydroxyl compound having at least two, and up to eight carbon atoms, which is preferably ethylene glycol; and the self-tanning composition may still further optionally contain an acidifying agent in amount sufficient to maintain the pH of said total composition at from about 3.5 to about 4.5, which is preferably sorbic acid. Cosmetologic products and methods of tanning are also provided.

18 Claims, No Drawings

SELF-TANNING DIHYDROXYACETONE FORMULATIONS HAVING IMPROVED STABILITY AND PROVIDING ENHANCED DELIVERY

CROSS-REFERENCE TO RELATED APPLICATIONS

This application is a continuation of Ser. No. 09/092,340 filed on Jun. 5, 1998, now abandoned which claims the benefits under 35 U.S.C. § 119(e) from provisional application Ser. No. 60/048,903 filed on Jun. 6, 1997.

FIELD OF THE INVENTION

The present invention is in the broader technical field relating to compositions for the topical application of active agents to the skin with sufficient penetration to be efficacious. Such active agents can be cosmetic agents or therapeutic agents; thus, the disciplines of pharmacology and cosmetology are involved. The present invention is, further, in the narrower technical field relating to cosmetic compositions where the active agent is a sunless tanning compound, in particular dihydroxyacetone, which is delivered by topical application of a cosmetic product formulation containing dihydroxyacetone to the skin of a user of said product. In this narrower technical field, it is appreciated that desirable product formulations have sufficient stability and skin penetration to provide an even tan of the desired color in a timely fashion.

BACKGROUND OF THE INVENTION

The prevailing cultural esthetic among fair-skinned persons in many countries and places is to have a skin which is tanned, i.e., which has a light yellowish brown or even deeper brown color produced by exposure to the sun or to an artificial source of ultraviolet light. The tanning of the skin is produced as a result of the darkening of preformed melanin, accelerated formation of new melanin, and retention of melanin in the epidermis as a result of retardation of keratinization. The darkening of existing melanin, possibly caused by oxidation and referred to as the Meirowsky phenomenon, begins within a few seconds of exposure to long-wave ultraviolet light and is complete within minutes up to a few hours, depending on the individual involved.

For those many individuals who wish to achieve a tanned skin, the most readily available means for doing so is by exposure of their skin to natural sunlight. However, this method carries with it certain hazards, chief among which is the risk of sunburn, i.e., actual injury to the skin produced by excessive exposure to ultraviolet rays. The injury is accompanied by erythema, tenderness, and sometimes blistering. Furthermore, excessive exposure to ultraviolet radiation is considered by the medical community to be a leading factor in the oncogenesis of melanomas and other skin cancers, as well as an accelerating agent in the aging of the skin, particularly its tendency to sag and wrinkle. In order to mitigate or prevent such excessive exposure, such individuals will usually seek the protection of various sunscreen products, which contain sunscreen agents that act either by absorbing the ultraviolet radiation or by reflecting incident light. Sunscreen products also provide the user with other protections and benefits which are desirable, such as those available from skin moisturizing, protective and healing compounds, anesthetic and anti-inflammatory agents, etc. Certain embodiments of the present invention utilize such conventional sunscreen materials in order to achieve a product with the most universal appeal and with the greatest possible number of benefits to its users.

Where ultraviolet radiation is the source of skin tanning, it should be noted briefly that such electromagnetic radiation lies beyond the violet end of the spectrum, whence its name. Ultraviolet radiation lies between violet rays and roentgen or "X" rays, is characterized by wavelengths between 200 and 400 nm, and has powerful actinic and chemical properties. Over 99% of ultraviolet radiation has wavelengths between 320 and 400, and is referred to as ultraviolet A, or simply UVA. The remaining 1% of ultraviolet radiation comprises ultraviolet B, or UVB radiation, which has wavelengths between 290 and 320 nm. UVB causes sunburn and a number of damaging photochemical changes within cells, including damage to DNA, leading to premature aging of the skin, premalignant and malignant changes, and a variety of photosensitivity reactions. Wavelengths between 200 and 290 nm characterize ultraviolet C radiation, or UVC, all of which is filtered out by the ozone layer and does not reach the earth's surface. Many persons, in order to achieve a satisfactorily tanned skin but unable to take advantage of naturally occurring sunlight, have resorted to the use of artificial sources of ultraviolet light, which are also much easier to regulate with respect to the amount of ultraviolet radiation to which the skin is exposed, than is the case with natural sunlight. On the other hand, there are many persons who, for a variety of reasons, make use of so-called self-tanning or sunless product formulations in order to achieve a satisfactory tan.

For example, many persons have skin complexions which do not tan readily or evenly when exposed to sunlight, and many others suffer significant adverse side effects from sun exposure, including severe sunburn. For such people, once a tan is obtained, there is a great deal of interest in maintaining or extending the life of that tan, which will naturally dissipate over time as the layers of skin which actually comprise the tan become necrotic and are eventually sloughed off. All such persons would greatly benefit from access to any means of obtaining a tanned skin, or at least a skin having the appearance of a naturally tanned skin, which did not require being exposed to sunlight, with all of the attendant adverse effects which arise from such exposure to ultraviolet radiation. Accordingly, such persons in ever greater numbers have turned to so-called self-tanning or sunless product formulations in order to achieve a "tan" without going through the harsh medium of the sun. However, there are many other persons who, although not as severely affected by exposure to ultraviolet radiation, also have turned to self-tanning products as a way of achieving a more uniform tan, of obtaining a deeper tan with significantly less total exposure to sunlight, and of extending the natural life of the tan which they have acquired for themselves. For such persons, a suitable product is to be found in those embodiments of the present invention which combine the components of a self-tanning composition with the components of a sunscreen formulation.

Self-tanning agents and formulations of various types and compositions are known in the art. For example, sunless tanning agents which have been discovered and used heretofore include dihydroxyacetone (DHA), glyceraldehyde (glycerol aldehyde) and related alcohol-aldehydes, various indoles and imidazoles and their derivatives, and pigmentation agents approved for use with humans, e.g., methoxsalen and trioxsalen. Dihydroxyacetone in particular is currently the self-tanning agent most widely used, and it has been known in the art for some time as an artificial tanning agent for use on the human epidermis. As used hereafter, the term "dihydroxyacetone" will be used to mean not only that specific composition of matter, but all of the other species described further herein which may be substituted for dihydroxyacetone in accordance with the objectives herein enumerated, whether with better or poorer results as measured by the several criteria also further below-described in more detail.

It has been widely postulated in the art that dihydroxyacetone achieves this effect by reacting with various skin proteins and amino acids to produce a tan-colored reaction product. Dihydroxyacetone has been used in a number of self-tanning formulations over the years combined, e.g., with colorants and sunscreen agents. Dihydroxyacetone, which may also be named as 1,3-dihydroxy-2-propanone, has the following structural formula:

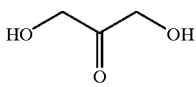
(I)

which corresponds to a elementary formula of $C_3H_6O_3$ and a molecular weight of 90.08. Dihydroxyacetone is a crystalline powder which is fairly hygroscopic and has a melting point of about 75–80° C. It has a characteristic odor. The normal form in which dihydroxyacetone exists is a dimer, which is slowly soluble in 1 part water and 15 parts ethanol. However, when dihydroxyacetone is freshly prepared it reverts rapidly to the monomer form, which is very soluble in water, ethanol, ether and acetone.

As already mentioned, dihydroxyacetone is probably the most wisely used commercially of all self-tanning agents, and it is the key active ingredient in numerous self-tanning products which have achieved solid market success. The precise mechanism by which dihydroxyacetone causes the self-tanning reaction was studied by Bobin et al. and reported in *J. Soc. Cosmet. Chem.*, 35, 265–272, August 1984. They studied the Maillard reaction of dihydroxyacetone with various amino acids found naturally in the hydrolipid pellicle and first layers of the stratum corneum of the skin. The Maillard reaction is one between the amino groups of amino acids, peptides or proteins with the "glycosidic" hydroxyl group of sugars, ultimately resulting in the formation of brown pigments. This reaction is also referred to commonly as the "browning" reaction, since this same reaction takes place when various foodstuffs are browned by heating during the process of their preparation for eating.

However, despite such wide use and market acceptance, dihydroxyacetone suffers from several notable drawbacks which have both prevented products containing it from obtaining even wider market penetration, and precluded the production of a cosmetic product formulation with all of the optimum characteristics desired by the ultimate consumer. One of these notable drawbacks is an unacceptably short shelf life. Dihydroxyacetone possesses a number of chemical and physical properties which place significant inherent constraints on its use. Dihydroxyacetone in the monomer form is highly soluble in water, which thereby exposes it to the action and affects of various agents, transports it into many unintended environments, and makes its isolation difficult. The substantial oxidizing capacity of dihydroxyacetone, which is the ultimate mechanism by which it presumably operates to produce a "tan", is a serious problem facing the cosmetic formulator or other artisan, since it can lead not only to undesired activity once applied to the skin of the ultimate consumer, but can also lead to difficulties in terms of its interaction with the other components with which it is formulated. Further, dihydroxyacetone does not possess a stable pH in solution, but is, rather, subject to a shifting pH which makes its formulation and ultimate use environment problematic to manage. Further still, dihydroxyacetone is especially sensitive to the degradative activities of bacteria and other microorganisms, against the attacks of which it must be protected, both in its inceptive formulation, as well as in its eventual use environment.

A major result of the above-described properties of dihydroxyacetone is its degradation upon standing, which is likely to take place while the product containing it is in the possession of the ultimate consumer, if not even before purchase, while still in transit. This abbreviated shelf life has required heretofore that products containing dihydroxyacetone be used soon after preparation, and that said products be stored under conditions optimized with regard to temperature and relative humidity so that the progress of degradation could at least be delayed. Nevertheless, the proportion of dihydroxyacetone remaining active in said products has been found to rapidly diminish with time. In addition to this loss of activity, the result of the chemical and physical degradation of dihydroxyacetone is the production of undesirable discoloration as well as the formation of disagreeable odors.

Another significant drawback of dihydroxyacetone, which is not, however, related to its instability, is the inherent and unpleasant odor which results from the reaction of dihydroxyacetone and those components of the skin with which it comes in contact during the self-tanning process. Accordingly, in order to address and overcome all of the above-described challenges posed by the properties of dihydroxyacetone, the artisan of ordinary skill in preparing cosmetic and therapeutic products has been forced to exercise all of the formulation skills possessed by said artisan. The result, however, has not been the discovery of a totally successful product up until the time that the present invention was made as described further herein.

BRIEF DESCRIPTION OF THE RELEVANT ART

Protecting the skin from the adverse effects of exposure to ultraviolet radiation has long been of concern in the art to which the present invention pertains. For example, Mansor, U.S. Pat. No. 3,019,165 relates to a pharmaceutical preparation for oral administration which prevents, counteracts, or relieves the effects on human skin and subcutaneous tissues of overexposure to sunlight. The preparation comprises p-aminobenzoic acid (PABA) in combination with an antihistaminic agent and a suitable salicylate, e.g., aspirin. The preparation is said to promote tanning of the skin on exposure to sunlight. Further, Majeti U.S. Pat. No. 4,098,881 is concerned with compositions containing conjugated dienes in combination with a topical skin compatible surfactant containing carrier which are used to control the chronic effects of prolonged exposure to sunlight.

In addition to protecting the skin from exposure to ultraviolet radiation, the art has also been concerned with treating the skin for conditions which might be associated with such exposure, e.g., dryness. For example, Musher U.S. Pat. No. 4,454,159 concerns preparations for treating irritated, pruritic and dry skin which contain a combination of lipids/lipoids comprising glycerol trioleate and other glyceride oils of certain fatty acids, tocopherol, squalene, collagen protein, a humectant, and isopropyl palmitate. Chaussee U.S. Pat. No. 4,970,220 relates to a skin conditioning cosmetic composition having enhanced conditioning and protection against dryness, compatible with personal care, topical drug and insect repellant compositions, comprising a panthenyl moisturizer, i.e. dl-panthenol, and an emollient which includes a polyhydric alcoholic humectant, preferably glycerol, and a polyether derivative, preferably a copolymer of polyethylene glycol and polypropylene glycol having a molecular weight of from 1000 to 2000. Sun screen additives, among other active agents are mentioned as includable in the cosmetic composition. Also, Ser and Miguel U.S. Pat. No. 5,437,859 is concerned with conferring hydrating characteristics to cosmetic or pharmaceutical solid fatty products, e.g., lip sticks, and discloses a process for the preparation of stable, anhydrous solid dispersions comprising preferably from 40 to 85% of a fatty body and preferably from 8 to 25% of a dispersed polyhydric alcohol. The polyhydric alcohol has from 2 to 8 carbon atoms and from 2 to 6 hydroxyl functions and includes, e.g., ethylene glycol, glycerin and 1,2-propane diol. Other additives typical for such cosmetic formulations are also described.

However, the present invention is concerned in particular with that segment of the art to which it pertains which has been concerned with providing artificial or self-tanning compositions as a means of protecting the skin. Such compositions, nevertheless, must overcome many of the constraints placed on the makeup of ordinary protective compositions, and have even been used in combination therewith, as is contemplated with the present invention. For example, Vanlerberghe and Rosenbaum U.S. Pat. No. 3,940,477 relates to a class of aminated γ-dialdehyes which may be used in cosmetic compositions to produce artificial tanning of the skin. McShane U.S. Pat. No. 4,434,154 relates to an artificial tanning and ultraviolet screening cosmetic composition which is stable after prolonged storage comprising 2.5 to 7.5% by weight of total composition of dihydroxyacetone, octyl dimethyl p-aminobenzoic acid, water, oil and surfactant. The compositions are oil-in-water emulsions and the surfactant is a sodium ($C_8$–$C_{16}$)alkyl sulfate, e.g., sodium lauryl sulfate. Ziegler and Crotty U.S. Pat. No. 5,232,688 concerns a self-tanning cosmetic compositions containing an α-hydroxy substituted ketone or aldehyde, preferably dihydroxyacetone, and a polyacrylamide preferably cross-linked and having a molecular weight of from 1000 to 5,000,000 for thickening, providing nonstreaking performance and improving low odor maintenance. Optionally, propylene glycol is advantageously incorporated in amounts of 15%, preferably between about 25 and 90%, in order to improve color intensity on the skin. Barnett and Lowry U.S. Pat. No. 5,268,166 relates to the application of a color cosmetic composition to the skin by means of electrostatic spraying in which artificial tanning materials containing dihydroxyacetone are included among the types of cosmetic compositions which may be utilized in this manner. Many of the additives used in these color cosmetic compositions function to make the compositions electrostatically sprayable, or to give the compositions certain desired properties when applied. Crotty and Ziegler U.S. Pat. No. 5,302,378 relates to a self-tanning composition containing, e.g., dihydroxyacetone in combination with an anionic silicone polyol such as dimethicone copolyol phosphate which prevents streaking, and at least 15% of propylene glycol to improve color intensity. Durand U.S. Pat. No. 5,458,872 is concerned with a method for protecting and stabilizing dihydroxyacetone which comprises enclosing at least a portion of the dihydroxyacetone in dimer form in a watertight composition which releases the dihydroxyacetone upon application. The watertight composition, which protects the dihydroxyacetone from water, oxidation and thermal effects, comprises a mixture of water insoluble polymers, e.g., vinylidene polychloride, copolymers of dimethylaminoethylmethacrylate, cellulose acetate, nitrocellulose, and ethyl cellulose, and optionally oily fats in the form of a mixture of monoglycerides, diglycerides, and triglycerides of fatty acids having a chain length between $C_9$ and $C_{22}$. Lentini and Zecchino U.S. Pat. No. 5,514,367 relates to self-tanning cosmetic compositions comprising dihydroxyacetone and at least one cyclodextrin, i.e., a natural cyclic oligosaccharide of six (α-), seven (β-) or eight (γ-) glucose residues, cycloamylose and cycloglucans which are naturally occurring clathrates, by means of which the cosmetic composition is rendered more stable as evidenced by longer storage life, has a reduced odor under storage and use, and has a reduction in the odor caused by the reaction of the dihydroxyacetone with the skin. Tanner and Robinson U.S. Pat. No. 5,514,437 relates to dihydroxyacetone artificial tanning compositions having improved stability which contain from 0.025% to 5% of a salt selected from metabisulfite salts, sulfite salts, and hydrogen sulfite salts, and mixtures thereof, as the stabilizing agent.

The compositions of the present invention, in addition to the below-described essential components thereof, contain a number of additional ingredients which, while optional, are nevertheless advantageous to include for the beneficial properties which they confer on said compositions. Said ingredients or similar additives have sometimes been employed heretofore in the art. For example, Walther and Stein, U.S. Pat. No. 3,281,374 concerns a process for the preparation of water-in-oil emulsions with the aid of polymeric higher fatty alcohols as the sole emulsifying agents, which results in a stable, creamy to pasty, colorless and odorless product able to absorb above 90% of water and rapidly absorbed by the skin. The monomers used to make the polymeric higher fatty alcohols have, e.g., from 12 to 24 carbon atoms and a terminal primary hydroxyl group. Lachampt et al. U.S. Pat. No. 3,489,690 is concerned with emulsifiers for preparing stable and irreversible water-in-oil emulsions for cosmetic use which provide hydration to the corneal layer of the skin as well as facilitating penetration of the emulsion products into the skin. The emulsifier is an oxypropylenated-oxyethylenated alcohol having a linear saturated alkyl radical of from 12 to 20 carbon atoms. A cosmetic formulation comprising a sunburn preventing cream is disclosed which contains an ultraviolet ray filter and an emulsifier of the formula: $C_{18}H_{37}$—[$OC_3H_6$]$_{6.5}$—[$OCH_2CH_2$]$_2$—OH. Dumoulin U.S. Pat. No. 3,975,294 is concerned with a surface active composition to be used as an emulsifier with diorganopolysiloxanes to form transparent micro-emulsions. Vanlerberghe and Sebag U.S. Pat. No. 4,303,639 relates to a class of 1,2-alkanediols which are colorless, odorless and miscible with oils conventionally used in cosmetic preparations, and which provide lubricity, ease of application, and good spreadability without an oily or greasy feel. Calvo et al. U.S. Pat. No. 4,466,955 concerns skin bleaching compositions based on hydroquinone using an anhydrous cosmetic carrier comprising polypropoxylated and polyethoxylated fatty ethers. Murray et al. U.S. Pat. No. 4,810,489 relates to high oil phase pharmaceutical vehicles in the form of an emulsion system comprising 35% to 65% oil phase, 1% to 10% of an alkylated polyvinylpyrrolidone copolymer, and an emulsifier.

The art has also explored combinations of self-tanning compositions and other active agents. For example, Kurz et al. U.S. Pat. No. 5,569,460 relates to a skin-coloring preparation comprising a hydroxycarbonyl compound, e.g., dihydroxyacetone, and at least one colorant which adheres to the skin and is preferably an organic dye which adheres by physical, rather than chemical bonding, e.g., red solorant and eosin derivatives. Solvents are selected from short- and long-chain monoalcohols, polyalcohols, alkylene glycols, etc. Bloom and Deckner U.S. Pat. No. 5,614,178 relates to pharmaceutical compositions for topical application having enhanced penetration through the skin comprising an active agent, including self-tanning agents, e.g., dihydroxyacetone, a high molecular weight crosslinked cationic polymer of dialkylaminoalkyl acrylate and methacrylate and a vinylic monomer, a high or low hydrophilic lipophilic balance (HLB) non-ionic surfactant, e.g., stearic acid ethoxylated with 1 mole of ethylene oxide (steareth-1), and an alkoxylated ether, e.g., polyoxypropylene butyl ether, having about 14 propylene oxide units incorporated in its structure.

Despite many previous attempts in the art to overcome the disadvantageous properties of dihydroxyacetone, as reflected in the disclosures of the above-discussed patents, none have been successful and none of them has arrived at the approach and the solution to these problems which comprise the present invention and which are described in more detail further below.

SUMMARY OF THE INVENTION

In its broadest aspects, there is provided in accordance with the present invention a composition comprising three components: (1) from about 0.5% to about 20.0% by weight, based on total weight of said composition, of a self-tanning skin coloring agent subject to chemical instability; (2) from about 2.0% to about 40.0% by weight, based on total weight of said composition of a polyethoxyglycol, preferably ethoxydiglycol; and (3) from about 0.1% to about 15.0% by weight, based on total weight of said composition, of a polyol comprising a polyhydric compound having at least three hydroxyl groups and at least three carbon atoms. The polyol forming one of the three components of said composition comprises one or more members independently selected from the group consisting of 1,2,6-hexanetriol, isopropylidene glycerol, polyoxyethylene sorbitols, glycerin (glycerol), diglycerin, erythritol, mannitol, xylitol, D and L-sorbitol, glucose, fructose, galactose, mannose, sucrose, lactose, trehalose, maltose and inositol; and said polyol is preferably D-sorbitol, D-mannitol, or inositol.

There is further provided the above-described composition in which the self-tanning skin coloring agent subject to chemical instability is preferably an α-hydroxy aldehyde or ketone, and more preferably is dihydroxyacetone, and is most preferably present in an amount of from about 4.0% to about 6.0% by weight, based on the total weight of said composition. Most preferably in said composition, the amount of polyethoxyglycol, preferably ethoxydiglycol is from about 14.0% to about 25.0% by weight, based on the total weight of said composition. The polyol employed in said composition is preferably sorbitol, and it is most preferably used in an amount of from about 0.5% to about 1.5% by weight, based on the total weight of said composition.

In accordance with other narrower, but no less preferred aspects of the present invention there is provided a composition comprising four components: the above-described components (1) through (3), comprising a self-tanning skin coloring agent subject to chemical instability, most preferably dihydroxyacetone; polyethoxyglycol, preferably ethoxydiglycol; and a polyol, most preferably sorbitol, as above-described; and (4) a water soluble dihydroxyl (diol) compound having at least two, and up to eight carbon atoms, preferably from two to five carbon atoms, present in an amount of from about 0.1% to about 8.0%, most preferably from about 0.4% to about 2.0% by weight, based on total weight of said composition. Preferably, said water soluble dihydroxyl (diol) compound will be one or more members selected from the group consisting of ethylene glycol; diethylene glycol; triethylene glycol; water soluble polyethylene glycols; propylene glycol, i.e., 1,2-propanediol, 1,3-propanediol, and 2-methyl-1,3-propanediol; dipropylene glycol; water soluble polypropylene glycols; butylene glycol, i.e., 1,2-butanediol, 1,3-butanediol, and 1,4-butanediol; pentanediols; and hexylene glycols including 1,6-hexanediol and 2-ethyl-1,3-hexanediol.

Further in accordance with still other narrower, but no less preferred aspects of the present invention there is provided a composition comprising five components: the above-described components (1) through (4), comprising a self-tanning skin coloring agent subject to chemical instability, most preferably dihydroxyacetone; polyethoxyglycol, preferably ethoxydiglycol; a polyol, most preferably sorbitol; and a water soluble dihydroxyl (diol) compound having preferably from two to five carbon atoms, e.g., propylene glycol and butylene glycol; and (5) an acidifying agent in amount sufficient to maintain the pH of the total composition at from about 3.5 to about 4.5, preferably about 4.0, said acidifying agent preferably being a mild organic acid such as acetic, adipic, anisic, benzoic, boric, carbonic, cinnamic, citric, diphosphonic, formic, fumaric gallic, glutaric, glycolic, lactic, maleic, malic, malonic, oxalic, phthalic, propionic, pyrogallic, pyruvic, salicylic, succinic, tartaric, or vanillic acid. Preferably, the acidifying agent will be selected from the group consisting essentially of sorbic acid, acetic acid, maleic acid, citric acid and fumaric acid. The precise amount depends upon both the strength and the concentration of the acidifying agent utilized, but will generally be in an amount of from about 0.01% to about 0.50% by weight, based on the total weight of said composition, preferably from about 0.02% to about 0.40% by weight, more preferably from about 0.03% to about 0.30% by weight, and most preferably from about 0.04% to about 0.20% by weight, based on the total weight of said composition.

The present invention also provides the above-described composition as a cosmetologic product for application to the hair, nails or skin of a subject for the purpose of tanning, coloring and/or darkening the same, wherein the remaining portion of said composition comprises a cosmetologically acceptable carrier. The cosmetologically acceptable carrier includes one or more members independently selected from the group consisting of acidifying and alkalizing agents; aerosol propellants; antimicrobial agents including antibacterial, antifungal and antiprotozoal agents; antimicrobial preservatives; antioxidants; buffering agents; chelating agents; coloring additives including dyes and pigments; dermatologically active agents; dispersing agents; emollients; emulsifying agents including emulsifying and stiffening agents and emulsion adjuncts; excipients; humectants; ointment bases; penetration enhancers; perfumes and fragrances; preservatives; sequestering agents; solvents; stabilizers; stiffening agents; sugars; sunscreen agents; surfactants; suspending agents; thickening agents; vehicles; viscosity-increasing agents; wetting agents; and wetting and/or solubilizing agents. In particular, there is provided a cosmetologic self-tanning product comprising dihydroxyacetone, ethoxydiglycol, sorbitol, and a sunscreen agent, especially otocrylene.

In accordance with the present invention there is further provided a method of tanning, coloring or darkening the hair, nails and/or skin of a subject comprising applying thereto an amount of the above-described cosmetologic product sufficient to tan, color, or darken said hair, nails and/or skin of said subject to which it is applied to the extent desired by said applicant.

In accordance with the present invention there is still further provided a method for preparing the above-described cosmetologic product wherein said product is an aqueous solution, comprising the steps, carried out sequentially or simultaneously, of (1) combining the water, dihydroxyacetone, ethoxydiglycol, polyol, optionally dihydroxyl compound, and optionally acidifying agent components of said product, optionally together with chelating agents, sequestering agents, antimicrobial preservatives, and/or antioxidants which are desired, optionally with a solvent therefor; and thereafter optionally (2) adding a perfume or fragrance which is desired optionally with a solvent therefor; (3) adding vitamins, nutrients, penetration enhancing agents, coloring additives, sunscreen agents, and/or other dermatologically active agents which are desired, optionally with a solvent therefor; and (4) adding antimicrobial preservatives which are desired, optionally with a solvent therefor.

There is also further provided a method for preparing the above-described cosmetologic product wherein said product is an emulsion, inverse emulsion, or suspension, comprising the steps, carried out sequentially or simultaneously, described further below.

In accordance with the present invention there is provided a composition comprising:

(1) from about 0.5% to about 20.0% by weight, based on the total weight of said composition, of an α-hydroxy aldehyde or ketone of the formula:

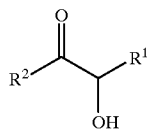

(II)

wherein $R^1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(\odot O)$; and $R^2$ is H or $CH_2OH$;

(2) from about 2.0% to about 40.0% by weight, based on the total weight of said composition of a polyethoxyglycol of the formula:

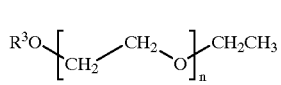

(III)

wherein n is an integer of from 2 to 6; and $R^3$ is H, $(C_1–C_6)$alkyl, or phenyl;

(3) from about 0.1% to about 15.0% by weight, based on the total weight of said composition, of a polyol comprising a polyhydric compound having at least three hydroxyl groups and at least three carbon atoms, preferably comprising one or more members independently selected from the above-enumerated group of such polyols;

(4) from about 0.1% to about 8.0% by weight, based on the total weight of said composition, of a dihydroxyl compound having from two to eight carbon atoms, preferably comprising one or more members independently selected from the above-enumerated group of such dihydroxyl compounds; and (5) an acidifying agent in amount sufficient to maintain the pH of the total composition at from about 3.5 to about 4.5.

Still further in accordance with the present invention there is provided a preferred composition as above-described comprising:

(1) from about 4.0% to about 6.0% by weight, based on the total weight of said composition, of dihydroxyacetone;

(2) from about 14.0% to about 25.0% by weight, based on the total weight of said composition of ethoxydiglycol;

(3) from about 0.5% to about 1.5% by weight, based on the total weight of said composition, of D-sorbitol;

(4) from about 0.4% to about 2.0% by weight, based on the total weight of said composition, of propylene glycol and butylene glycol; and (5) from about 0.04% to about 0.20% by weight, based on the total weight of said composition, of sorbic acid.

The present invention also provides the above-described compositions as cosmetologic products for application to the hair, nails or skin of a subject for the purpose of tanning, coloring and/or darkening the same, wherein the remaining portion of said composition comprises a cosmetologically acceptable carrier as above-described.

DETAILED DESCRIPTION OF THE INVENTION

The present invention provides a composition comprising from about 0.5% to about 20.0% by weight, based on total weight of said composition, of a self-tanning skin coloring agent subject to chemical instability which is preferably an α-hydroxy aldehyde or ketone, and more preferably is dihydroxyacetone. The composition of the present invention has improved stability with regard to the self-tanning skin coloring agent component, especially dihydroxyacetone in that the remaining key components of the composition serve to overcome the chemical instability to which the self-tanning skin coloring agent is subject. These key components of the composition of the present invention are effective alone or in combination to diminish or even prevent degradation of the self-tanning skin coloring agent, especially dihydroxyacetone component.

The self-tanning skin coloring component is always used in combination with a polyethoxyglycol, especially ethoxydiglycol in the compositions of the present invention. The additional key component which is required at a minimum in said compositions in order to counteract the chemical instability of the self-tanning skin coloring component is a polyol. The polyol component of said composition is effective in this regard when used alone. However, the reversal of said chemical instability is even more pronounced when the polyol component is used together with the further key component comprising a dihyroxyl compound. Moreover and surprisingly, said reversal of chemical instability is still further pronounced when the polyol and dihydroxyl compound components are used together with the still further key component comprising an acidfying agent.

The basic causes of the chemical instability of the self-tanning skin coloring agent, especially where said agent is dihydroxyacetone, are still unknown even after investigation of this phenomenon. It is known that when the self-tanning skin coloring component and the polyethoxyglycol component are mixed together with water, the pH of the formulation mixture is about 4.0, at least initially. However, inexplicably the pH of the formulation mixture soon begins to drop, i.e., the mixture becomes more acidic and the self-tanning skin coloring agent, especially dihydroxyacetone, becomes unstable. The formulation mixture is observed to disintegrate with the formation of organic acids and formalin, leading to the creation of disagreeable odors and unacceptable colors in the formulation mixture.

It is theorized that the key components of the compositions of the present invention result in ketalization of the hydroxyl groups of the self-tanning skin coloring agent, especially dihydroxyacetone, making it more resistant to chemical attack. It is also known that dihydroxyacetone occurs naturally as a dimer, but that only the monomeric form has self-tanning skin coloring properties. It is also possible that the stabilization of the self-tanning skin coloring agent by the components of the compositions of the present invention is achieved by hydrogen bonding between said agent and said components. Regardless of the manner in which it is achieved, however, this stabilization result is achieved whether the source of the degradation is based on temperature, hydrolysis, pH, microbial attack, or some combination of these factors. Further, it has been observed that in the stabilized compositions of the present invention that the self-tanning skin coloring agent gradually disappears over time, but that the formulation mixture retains its integrity and remains stable.

The preferred self-tanning skin coloring agent, dihydroxyacetone, 1,3-dihydroxy-2-propanone, may be represented by the following general structural formula:

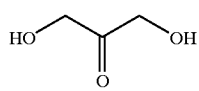

(I)

Dihydroxyacetone which corresponds to an elementary formula of $C_3H_6O_3$. Dihydroxyacetone is a crystalline powder which is fairly hygroscopic, and the normal form in which it exists is a dimer, which is slowly soluble in 1 part water and 15 parts ethanol. However, when dihydroxyacetone is freshly prepared it reverts rapidly to the monomer form, which is very soluble in water, ethanol, ether and acetone. This high degree of water solubility is one of several notable drawbacks from which dihydroxyacetone suffers and which has precluded up until the present invention the preparation of a cosmetic product formulation containing dihydroxyacetone which possesses all of the optimum characteristics desired by the ultimate consumer.

Thus, one of the serious disadvantages of dihydroxyacetone is an unacceptably short shelf life. In fact, dihydroxyacetone is characterized by properties which place significant inherent constraints on its use. Dihydroxyacetone in the monomer form is highly soluble in water. While this is a desirable property with respect to preparing formulations with dihydroxyacetone, it also creates a problem because it thereby exposes dihydroxyacetone to the action and affects of various agents, transports it into many unintended environments, and makes its isolation difficult. One attempt in the art to overcome this undesirable property of dihydroxyacetone is disclosed in Durand U.S. Pat. No. 5,458,872 in which a method for protecting and stabilizing dihydroxyacetone relies on encapsulating it in a watertight composition comprising a water-insoluble polymer, e.g., ethyl cellulose.

Another serious problem facing the cosmetic formulator or other artisan attempting to devise a useful composition containing dihydroxyacetone is the substantial oxidizing capacity of dihydroxyacetone, since it can lead not only to undesired activity once applied to the skin of the ultimate consumer, but can also lead to difficulties in terms of its interaction with the other components with which it is formulated. Dihydroxyacetone is also characterized by an unstable pH in solution, and its shifting pH will vary from as high as about 6.0 to as low as about 2.0. At the lower pH's especially, dihydroxyacetone becomes very unstable, which makes its formulation and ultimate use environment problematic to manage. The optimum pH for stability of dihydroxyacetone is about 4.0; accordingly the compositions of the present invention have been buffered to pH 4.7. Another source of instability in dihydroxyacetone is its particular sensitivity to the degradative activities of bacteria and other microorganisms. It is thus necessary to protect dihydroxyacetone against such attack, both at the time it is incorporated in a formulation for eventual use, as well as at the time when such use actually takes place.

As used herein, the term "dihydroxyacetone" is sometimes broadly inclusive, especially of structurally related compounds. However, the more appropriate generic expression for such compounds is "α-hydroxy aldehydes and ketones. Nevertheless, the present invention also includes the use of structurally dissimilar compounds, which are included within the rubric "self-tanning skin coloring agents". All such agents are similarly useful in producing or inducing the artificial tanning process in human skin, as described herein, and are thus contemplated to be within the scope of the present invention. Dihydroxyacetone itself may be represented by the following general structural formula:

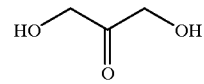

(I)

Dihydroxyacetone

A number of other compounds are already known in the art as capable of producing or inducing the same artificial tanning process in human skin as is produced or induced by dihydroxyacetone. Some of these are structurally similar to dihydroxyacetone and include, inter alia, the following:

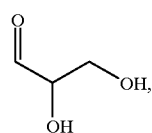

(IV)

Glyceraldehyde

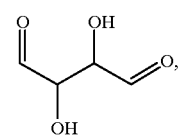

(V)

2,3-Dihydroxy-succindialdehyde

-continued

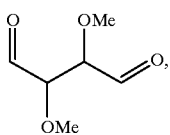

2,3-Dimethoxy-
succindialdehyde (VI)

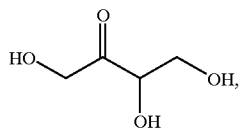

Erythrulose (VII)

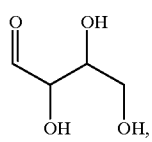

Erythrose (VIII)

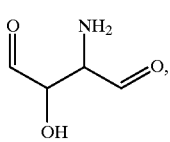

2-Amino-3-hydroxy-
succindialdehyde and (IX)

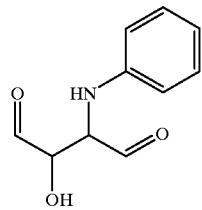

2-Benzylamino-3-hydroxy-
succindialdehyde (X)

Accordingly, in a preferred embodiment of the present invention there is provided a composition comprising from about 0.5% to about 20.0% by weight, based on total weight of said composition, of an α-hydroxy aldehyde or ketone of the formula:

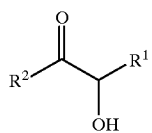

(II)

wherein $R^1$ is H, $CH_2OH$, $CHOHCH_2OH$, $CH(OH)CH(=O)$, $CH(OCH_3)CH(=O)$, $CH(NH_2)CH(=O)$, or $CH(NH-Phenyl)CH(=O)$; and $R^2$ is H or $CH_2OH$. The above formula represents dihydroxyacetone when $R^1$ is H and $R^2$ is $CH_2OH$. Preferably, the composition of the present invention will contain from about 1.0% to about 15.0% by weight, more preferably from about 2.0% to about 10.0% by weight, more preferably still from about 3.0% to about 8.0% by weight, and most preferably from about 4.0% to about 6.0% by weight, based on total weight of said composition, of a self-tanning skin coloring agent, preferably an α-hydroxy aldehyde or ketone of the above formula, and most preferably dihydroxyacetone.

It is well known in the art that the closest homolog to dihydroxyacetone, methyl glyoxal, has been identified as a metabolite or degradation product of dihydroxyacetone which is responsible for the development of discoloration in formulations containing dihydroxyacetone which have not been stabilized. Methyl glyoxal is also responsible for the production of an undesirable orange pigmentation when dihydroxyacetone is applied to the skin and is not present in a stabilized form. Accordingly, methyl glyoxal is not one of the compounds structurally similar to dihydroxyacetone which is contemplated to be a component of the compositions of the present invention. Methyl glyoxal may be represented by the following formula:

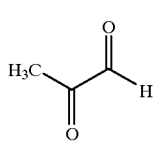

(XI)

Methyl glyoxal

Other self-tanning skin coloring agents which are structurally dissimilar to dihydroxyacetone but are still contemplated to be within the scope of the present invention with regard to the ability of the compositions of the present invention to improve their stability and enhance their efficiency, include, but are not limited to the following:

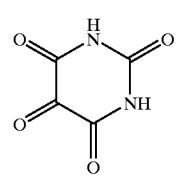

(XII)

Alloxan

It has been discovered in accordance with the present invention that, surprisingly, a significant and unexpected degree of stability can be conferred on cosmetological and pharmaceutical compositions containing self-tanning skin coloring agents, preferably α-hydroxy aldehydes or ketones, most preferably dihydroxyacetone, when such compositions additionally contain from about 2.0% to about 40.0% by weight, based on total weight of said composition of a polyethoxyglycol, perferably ethoxydiglycol, i.e., 2-(2-ethoxyethoxy)ethanol or Carbitol®. The term "ethoxydiglycol" is sometimes used herein as broadly inclusive of the polyethoxyglycols which in accordance with the present invention are components of a composition which confers improved stability and enhanced performance on the above-described self-tanning skin coloring agents, preferably α-hydroxy aldehydes and ketones. Said polyethoxyglycols are compounds which may be represented by the following general structural formula:

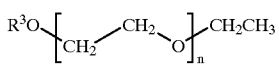

wherein n is an integer of from 2 to 6; and $R^3$ is H, $(C_1–C_6)$alkyl, or phenyl. In the case where n is 2 and $R^3$ is H, the resulting compound is ethoxydiglycol, which may be represented by the following formula:

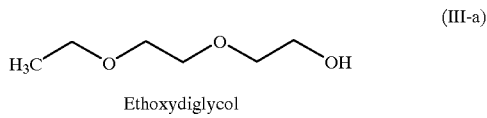

Ethoxydiglycol

Preferably, the amount of polyethoxyglycol, preferably diethoxyglycol which will be present in the compositions of the present invention will be from about 5.0% to about 35.0% by weight, more preferably from about 10.0% to about 30% by weight, more preferably still from about 12.0% to about 27% by weight, and most preferably from about 14.0% to about 25.0% by weight, based on total weight of said composition.

The broadest embodiment of the present invention comprises compositions which contain one key component in addition to the above-described self-tanning skin coloring agent and polyethoxyglycol. That essential element of the compositions of the present invention is a polyol. The term "polyol" as used herein is intended to mean a polyhydric compound having at least three hydroxyl groups and at least three carbon atoms. The upper limit of the number of carbon atoms which may be present is determined by the water solubility of such a candidate polyol and the compatibility thereof with the other components of the compositions of the present invention. It is preferred that the polyol forming a part of said composition of the present invention comprises one or more members independently selected from the group consisting of 1,2,6-hexanetriol, isopropylidene glycerol, polyoxyethylene sorbitols, glycerin (glycerol), diglycerin, erythritol, mannitol, xylitol, D and L-sorbitol, glucose, fructose, galactose, mannose, sucrose, lactose, trehalose, maltose, and inositol. The polyol component of the composition of the present invention is present in an amount of from about 0.1% to about 15.0% by weight, based on total weight of said composition. Preferably, the polyol is present in an amount of from about 0.2% to about 10.0% by weight, more preferably from about 0.3% to about 5.0% by weight, more preferably still from about 0.4% to about 3.0% by weight, and most preferably from about 0.5% to about 1.5% by weight, based on total weight of said composition.

The next broadest embodiment of the present invention comprises compositions which contain one further key component in addition to the above-described essential elements comprising a self-tanning skin coloring agent, polyethoxyglycol, and polyol. That optional but desirable additional element of the compositions of the present invention is a dihydroxyl compound. The term "dihydroxyl compound" as used herein is intended to mean a dihydric or diol compound having at least two carbon atoms and up to as many as eight carbon atoms, while it is preferred that said dihydric or diol compound have at least two carbon atoms and up to as many as five carbon atoms. It is more preferred that said dihydric or diol compound is one or more members selected from the group consisting of ethylene glycol; diethylene glycol; triethylene glycol; water soluble polyethylene glycols; propylene glycol, i.e., 1,2-propanediol, 1,3-propanediol, and 2-methyl-1,3-propanediol; dipropylene glycol; water soluble polypropylene glycols; butylene glycol, i.e., 1,2-butanediol, 1,3-butanediol, and 1,4-butanediol; pentanediols; and hexylene glycols including 1,6-hexanediol and 2-ethyl-1,3-hexanediol.

The next broadest, i.e., the least broad embodiment of the present invention comprises compositions which contain one still further key component in addition to the above-described essential elements comprising a self-tanning skin coloring agent, polyethoxyglycol, a polyol, and a dihydroxyl compound. That optional but desirable additional element of the compositions of the present invention is an acidifying agent in amount sufficient to maintain the pH of the total composition at from about 3.5 to about 4.5, preferably about 4.0. While use of an acidifying agent is optional in compositions of the present invention, it is contemplated that such use is a preferred embodiment of the present invention. It is theorized that the use of an acidifying agent improves the method of the present invention by moving the stabilization reaction with the self-tanning skin coloring agent, especially dihydroxyacetone forward, i.e., the equation of the reaction illustrated further above is moved further to the right, toward completion.

Acidifying agents which may be suitable for use in preparing the compositiions of the present invention will be apparent to the artisan instructed by the present description. It is preferabe, of course, to employ a mild organic acid such as acetic, adipic, anisic, benzoic, boric, carbonic, cinnamic, citric, diphosphonic, formic, fumaric gallic, glutaric, glycolic, lactic, maleic, malic, malonic, oxalic, phthalic, propionic, pyrogallic, pyruvic, salicylic, succinic, tartaric, or vanillic acid. More preferably, the acidifying agent will be selected from the group consisting essentially of sorbic acid, acetic acid, maleic acid, citric acid and fumaric acid. The precise amount depends upon both the strength and the concentration of the acidifying agent utilized, but will generally be in an amount of from about 0.01% to about 0.50% by weight, based on the total weight of said composition, preferably from about 0.02% to about 0.40% by weight, more preferably from about 0.03% to about 0.30% by weight, and most preferably from about 0.04% to about 0.20% by weight, based on the total weight of said composition To recapitulate, the present invention in its broadest embodiment is concerned with a composition comprising from about 0.5% to about 20.0% by weight of a self-tanning skin coloring agent, preferably an α-hydroxy aldehyde or ketone, most preferably dihydroxyacetone; from about 2.0% to about 40.0% by weight of a polyethoxyglycol, preferably diethoxyglycol; and from about 0.1% to about 15.0% by weight of a polyol comprising a polyhydric compound having at least three hydroxyl groups and at least three carbon atoms, all of said weight percentages being based on the total weight of said composition. These novel compositions of the present invention may be used for any purpose, but are particularly well suited for therapeutic and cosmetic applications. More particularly still, these novel compositions of the present invention provide self-tanning skin coloring cosmetic product formulations with optimal properties of storage stability which affords long shelf life and freedom from unwanted discoloration and disagreeable odors; enhanced penetration which provides a more rapid and uniform tanning process, as well as improved resulting color quality and increased resrulting color intensity; and application stability which avoids the formation of undesirable orange pigmentation when contacted with the skin and the formation of undesirable odors resulting from certain chemical reactions with the skin.

Accordingly, the present invention is especially concerned with providing a cosmetologic product for application to the hair, nails or skin of a subject for the purpose of tanning, coloring and/or darkening the same, comprising a composition as described immediately above wherein a remaining weight percent portion of said composition comprises a cosmetologically acceptable carrier. The individual components which together make up such a cosmetologically acceptable carrier are numerous and varied, but are also well known to the artisan of ordinary skill. Such an artisan is a person who has studied pharmaceutical, medicinal, or cosmetological chemistry and has an advanced degree in one or more of those fields and at least five years of working research experience in discovering new and useful pharmaceutical or cosmetological formulations. The components just referred to and their functions will be pointed out in turn in order that the compositions of the present invention and their uses may be made even more clear.

Vehicle—the vehicle, often referred to as the base for the cosmetologically acceptable carrier, may be any fluid material which is capable of delivering the other components of the composition to the skin with acceptable absorption of those components into the skin. The cosmetologically acceptable carrier may be in a number of different and convenient delivery forms. For example, the carrrier may be in the form of a spray or mist, aerosolized by means of a propellant or by mechanical means using ambient air; the carrier may be a semi-solid cream, lotion, gel or similar vehicle intended to be applied to the surface of the skin and thereafter forced into the deeper layers of the skin through the application of pressure and friction from rubbing, where the carrier and its components are absorbed by the skin; the carrier may be in the form of a liquid such as a solution, emulsion or suspension in which the carrier is a solvent for the other components of the overall composition, or else comprises the continuous phase of an emulsion in which the active components are the discontinuous phase, but also includes inverse emulsions in which the carrier is the discontinuous phase; or the carrier may be in the form of a solid such as a powder applied by dusting or spraying, a solid stick to be rubbed against the skin to which a portion of the solid adheres, or a mask applied as a flexible, formable material or as a liquid or gel which hardens to a solid by a process of solvent evaporation or crosslinking induced by heat, ultraviolet light or some other catalyzing agency.

The preferred cosmetologically acceptable carriers for use in the present invention are an aqueous solution in which a suitable viscosity has been achieved, or an oil-in-water emulsion in which the continuous aqueous phase contains those active agents which are water soluble, and the discontinuous oil phase contains those active agents of the overall composition which are oil soluble. The emulsion inverts upon application to the lipophilic surface of the skin, whereby the active agents are absorbed into the skin from both the continuous and discontinuous phases. Where the carrier is an aqueous solution, the water acting as solvent is preferably deionized water which contains inorganic ions in concentrations insufficient to interfere with the stability or functioning of the overall composition. The active agents in the composition, e.g., the dihydroxyacetone, ethoxydiglycol, and sorbitol are sufficiently water soluble to provide the desired final concentrations thereof, and the other components, described further below, are either sufficiently water soluble to be added directly to the aqueous solution, or else are insufficiently water soluble and are first dissolved in water miscible solvents in which they are sufficiently soluble, e.g., propylene and butylene glycol, after which the water miscible solvent solution is added to the aqueous solution.

Where the cosmetologically acceptable carrier is an oil-in-water emulsion, an oil or lipid phase is established by the addition of hydrocarbon and/or silicone solvents together with various emulsifying agents and aids to permit stable coexistence of the continuous and discontinuous phases. Whether aqueous solution or emulsion, the amount of water or aqueous carrier to be included in the compositions of the present invention will vary depending upon the desired consistency of the final product. By varying the amount of water, gelling agent, and/or surfactant present, it is possible to formulate a thick-flowing liquid or lotion, a semi-liquid thick cream, a paste, a stick, a gel, an alcoholic hydrogel, an emulsion, an alcoholic solution, or a formulation suitable for use in an aerosol. A consistent requirement of any such formulation, however, is that it can be uniformly spread on the skin and absorbed.

Into the vehicle of the cosmetologically acceptable carrier is introduced the desired pharmaceutically acceptable and cosmetologically acceptable additives whose compositions and functions are described in the below paragraphs.

Acidifying and Alkalizing Agents—are added to the composition largely to obtain a desired or predetermined pH. Acidifying agents include. e.g., acetic acid, glacial acetic acid, malic acid, and propionic acid. Stronger acids such as hydrochloric acid, nitric acid and sulfuric acid should be avoided. Alkalizing agents include, e.g., edetol, potassium carbonate, potassium hydroxide, sodium borate, sodium carbonate, and sodium hydroxide. However, alkalizing agents which contain active amine groups, such as diethanolamine and trolamine, not be used.

Aerosol Propellants—are required where the composition is to be delivered as a aerosol under significant pressure, and include, e.g., acceptable halogenated hydrocarbons such as dichlorodifluoromethane, dichlorotetrafluoroethane, and trichloromonofluoromethane; nitrogen; or a volatile hydrocarbon such as butane, propane, isobutane or mixtures thereof.

Antimicrobial Agents Including Antibacterial, Antifungal and Antiprotozoal Agents—are added where the composition will be applied to areas of the skin which are likely to have suffered adverse conditions or sustained abrasions or cuts which expose the skin to infection by bacteria, fungi or protozoa, and include, e.g., antimicrobial agents such as benzyl alcohol, chlorobutanol, phenylethyl alcohol, phenylmercuric acetate, potassium sorbate, and sorbic acid; and antifungal agents such as benzoic acid, butylparaben, ethylparaben, methylparaben, propylparaben, and sodium benzoate.

In a preferred embodiment of the present invention, benzyl alcohol in combination with methylparaben is used as the antimicrobial agent. The combination of these agents provides an antimicrobial action which is gentle and does not interfere with the actions of the other components of the compositions of the present invention. The combination of benzyl alcohol and methylparaben plays a nominal role, if any, in the stabilization of the self-tanning skin coloring agents, especially dihydroxyacetone, used in the compositions of the present invention. By contrast, antimicrobial agents often found in self-tanning commercial formulations comprise water-soluble compounds with active nitrogen atoms. However, it has been discovered that such compounds are troublesome because they undergo a Maillard reaction with the dihydroxyacetone to form different side products which have undesirable properties. Although sorbic acid may also be employed as an antimicrobial agent, its preferred use, as discussed further above, is as an acidifying agent in accordance with the present invention.

Antimicrobial Preservatives—are added to the compositions of the present invention in order to protect them against the growth of potentially harmful microorganisms, which usually invade the aqueous phase, but in some cases can also grow in the oil phase. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol. It is essential, of course, to select the preservative with a view toward possible incompatibilities between the preservative and other ingredients of the composition. For example, anitmicrobial preservatives which contain active amine groups are not suitable. These include, e.g., hydantoin derivatives, quaternary ammonium compounds and cationic polymers, imidazolidinyl urea, diazolidinyl urea, and trisodium ethylenediamine tetracetate (EDTA). Preservatives are preferably employed in amounts ranging from about 0.01% to about 2.0% by weight of the total composition.

Antioxidants—protect all of the ingredients of the composition from damage or degradation by oxidizing agents present in the composition itself, the use environment, or the skin to which the composition is being applied, and include, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols.

Buffering Agents—are typically used to maintain a desired pH of a composition once established, from the effects of outside agents and shifting equilibria of components of the composition. However, one of the advantages of the compositions of the present invention is that they are self-buffering and seldom require the addition of a buffering agent in order to maintain the desired pH. Nevertheless, in those rare instances where a buffering agent is added, it may be selected from among those familiar to the artisan skilled in the preparation of cosmetic formulation, e.g., calcium acetate, potassium metaphosphate, potassium phosphate monobasic, and tartaric acid.

Chelating Agents—help maintain the ionic strength of the composition and also serve a protective function in binding to and effectively removing a number of destructive compounds and metals, and include, e.g., edetate dipotassium, edetate disodium, and edetic acid.

Coloring Additives Including Dyes and Pigments—are especially useful adjuncts in the compositions of the present invention for the purpose of enhancing, toning, increasing the intensity, and changing the tanning color produced by the self-tanning agent, and include, e.g., caramel; 9-phenyl derivatives of 9-H-xanthen which are fluorescein derivatives of the formula:

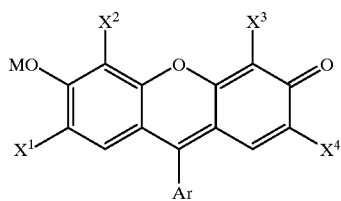
(XIII)

where $X^1$ to $X^4$ are each independently H, $NO_2$ or halo; M is H or an alkali metal; and Ar is phenyl substituted by a metal carboxylate and optionally up to four halogen atoms; furobenzopyranone derivatives of the formulas:

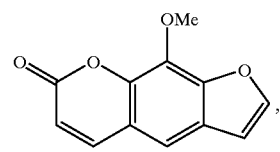
Methoxsalen
(XIV)

and

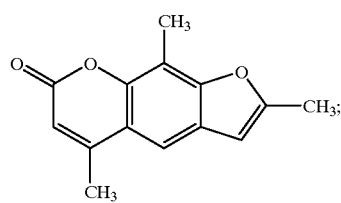
Trioxsalen
(XV)

Pigments must be chosen carefully to avoid unwanted catalysis of undesired side reactions in the compositions of the present invention. Thus, it would normally be unacceptable to select a metal oxide or other active salt such as black iron oxide, chromium oxides, yellow and red iron oxides, titanium dioxide, ultramarines (aluminosilicate polysulfides), manganese pyrophosphate, and ferric blue . . . . However, it is possible to use such pigments as carbon black and certain organic dyes such as cochineal carmine, azo dyes, and anthraquinone dyes; natural, colored cosmetically active substances which mask the hue produced by dihydroxyacetone or other self-tanning agent, such as the blue azulenes guajazulene and chamuzulene, the yellow flavanoids rutin and quercetin, erythrosin, bengal rose, phloxin, cyanosin, daphinin, eosin G, cosin 10B, and Acid Red 51.

Dermatologically Active Agents—are any one or more of the numerous and diverse known therapeutic agents applied to the skin for a dermatologically beneficial purpose, which include, e.g., wound healing agents such as peptide derivatives, yeast, panthenol, hexylresorcinol, phenol, tetracycline hydrochloride, lamin and kinetin; glucocorticosteroids for treating inflammation, e.g., hydrocortisone, dexamethasone, betamethasone, triamcinolone, fluocinolone and methylprednisolone; retinoids for treating acne, psoriasis, cutaneous aging, and skin cancer, e.g., retinol, tretinoin, isotretinoin, etretinate, acitretin, and arotinoid; immunosuppressive agents for treating inflammation, e.g., dapsone and sulfasalazine; antibacterial agents for treating mild acne, e.g., resorcinol, salicylic acid, benzoyl peroxide, erythromycin-benzoyl peroxide, erythromycin, and clindamycin, and for treating impetigo, e.g., mupirocin; antifungal agents for treating tinea corporis, tinea pedis, candidiasis and tinea versicolor, e.g., griseofulvin, azoles such as miconazole, econazole, itraconazole, fluconazole, and ketoconazole, and allylamines such as naftifine and terfinafine; antiviral agents for treating cutaneous herpes simplex, herpes zoster, and chickenpox, e.g., acyclovir, famciclovir, and valacyclovir; antihistamines for treating pruritis, atopic and contact dermatitis, and psoriasis, e.g., diphenhydramine, terfenadine, astemizole, loratadine, cetirizine, acrivastine, and temelastine; topical anesthetics for rerlieving pain, irritation and itching, e.g., benzocaine, lidocaine, dibucaine, and pramoxine hydrochloride; topical analgesics for relieving pain and inflammation, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Dispersing and Suspending Agents—include, e.g., poligeenan, povidone, and silicon dioxide, although povidone may cause Maillard side reactions and should be used with caution.

Emollients—are agents, preferably non-oily and water-soluble, which soften and sooth the skin, especially skin that has become dry because of excessive loss of water, and include, e.g., hydrocarbon oils and waxes such as mineral oil, petrolatum, microcrystalline wax, and polyethylene; triglyceride esters such as those of castor oil, cocoa butter, safflower oil, cottonseed oil, corn oil, olive oil, cod liver oil, almond oil, avocado oil, palm oil, sesame oil, squalene, and soybean oil; acetylated monoglycerides; ethoxylated glycerides such as ethoxylated glyceryl monostearate; methyl, isopropyl, butyl and other alkyl esters of $C_{10}$–$C_{20}$ fatty acids, such as hexyl laurate, isohexylpalmitate, decyl oleate, hexadecyl stearate, isopropyl isostearate, diisohexyl adipate, diisopropyl sebacate, lauryl lactate, myristyl lactate and cetyl lactate; alkenyl esters of $C_{10}$–$C_{20}$ fatty acids, such as oleyl myristate, oleyl stearate, and oleyl oleate; $C_{10}$–$C_{20}$ fatty acids, such as pelargonic, lauric, myristic, palmitic, stearic, isostearic, hydroxystearic, oleic, linoleic, ricinoleic, arachidic, behenic, and erucic acids; $C_{10}$–$C_{20}$ fatty alcohols, such as lauryl, myristyl, cetyl, hexadecyl, stearyl, isostearyl, hydroxystearyl, oleyl, linoleic, ricinoleyl, behenyl, erucyl, and 2-octyl dodecanol alcohols; fatty alcohol ethers which are ethoxylated $C_{10}$–$C_{20}$ fatty alcohols such as the lauryl, cetyl, stearyl, isostearyl, oleyl, and cholesterol alcohols having attached thereto from 1 to 50 ethylene oxide groups or 1 to 50 propylene oxide groups; ether-esters such as fatty acid esters of ethoxylated fatty alcohols; lanolin and derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, ethoxylated alcohols-esters, hydrogenated lanolin, ethoxylated hydrogenated lanolin, and ethoxylated sorbitol lanolin; polyhydric alcohol esters such as ethylene glycol mono- and di-fatty acid esters, diethylene glycol mono- and di-fatty acid esters, polyethylene glycol (200–600) mono- and di-fatty acid esters, propylene glycol mono- and di-fatty acid esters, polypropylene glycol 2000 mono-oleate, polypropylene glycol 2000 mono-stearate, ethoxylated propylene glycol monostearate, glyceryl mono- and di-fatty acid esters, polyglycerol poly-fatty acid esters, ethoxylated glyceryl monostearate, 1,3-butylene glycol monostearate, polyoxyethylene polyol fatty acid ester, sorbitan fatty acid esters, and polyoxyethylene sorbitan fatty acid esters; wax esters such as beeswax, spermaceti, myristyl myristate, and stearyl stearate; beeswax derivatives such as polyoxyethylene sorbitol beeswax; vegetable waxes such as carnauba and candelilla waxes; phospholipids such as lecithin and derivatives thereof; and sterols such as cholesterol and cholesterol fatty acid esters. However, emollients based on compounds which contain active amine groups are unsuitable. For example, amides such as fatty acid amides, ethoxylated fatty acid amides, and solid fatty acid alkanolamides should not be used.

Emulsifying Agents Including Emulsifying and Stiffening Agents and Emulsion Adjuncts—are used for preparing the oil-in-water emulsions forming part of the present invention, e.g., non-ionic emulsifiers such as $C_{10}$–$C_{20}$ fatty alcohols and said fatty alcohols condensed with from 2 to 20 moles of ethylene oxide or propylene oxide, ($C_6$–$C_{12}$)alkyl phenols condensed with from 2 to 20 moles of ethylene oxide, mono- and di-$C_{10}$–$C_{20}$ fatty acid esters of ethylene glycol, $C_{10}$–$C_{20}$ fatty acid monoglyceride, diethylene glycol, polyethylene glycols of MW 200–6000, polypropylene glycols of MW 200–3000, and particularly sorbitol, sorbitan, polyoxyethylene sorbitol, polyoxyethylene sorbitan, hydrophilic wax esters, cetostearyl alcohol, oleyl alcohol, lanolin alcohols, cholesterol, mono- and di-glycerides, glyceryl monostearate, polyethylene glycol monostearate, mixed mono- and distearic esters of ethylene glycol and polyoxyethylene glycol, propylene glycol monostearate, and hydroxypropyl cellulose.

However, emulsifying agents which contain active amine groups should not be used. Such agents typically include anionic emulsifiers such as fatty acid soaps, e.g., sodium, potassium and triethanolamine soaps of $C_{10}$–$C_{20}$ fatty acids; alkali metal, ammonium or substituted ammonium ($C_{10}$–$C_{30}$)alkyl sulfates, ($C_{10}$–$C_{30}$)alkyl sulfonates, and ($C_{10}$–$C_{20}$)alkyl ethoxy ether sulfonates. Other suitable emulsifying agents include castor oil and hydrogenated castor oil; lecithin; and polymers of 2-propenoic acid together with polymers of acrylic acid, both cross-linked with allyl ethers of sucrose and/or pentaerythritol, having varying viscosities and identified by product names carbomer 910, 934, 934P, 940, 941, and 1342. However, cationic emulsifiers having active amine groups should also be avoided, which would include those based on quaternary ammonium, morpholinium and pyridinium compounds. Similarly, amphoteric emulsifiers having active amine groups, such as cocobetaines, lauryl dimethylamine oxide and cocoylimidazoline, should not be used. Useful emulsifying and stiffening agents includecetyl alcohol and sodium stearate; and emulsion adjuncts such as oleic acid, stearic acid, and stearyl alcohol.

Excipients—include, e.g., laurocapram and polyethylene glycol monomethyl ether.

Humectants—are compounds which promote retention of moisture, thus often being referred to as moisturizers, and include, e.g., sorbitol, glycerin, glycereth 5 lactate, glycereth 7 triacetate, glycereth 7 diisonanoate, hexanetriol, hexylene glycol, propylene glycol, alkoxylated glucose, D-panthenol and derivatives thereof, and hyaluronic acid. However, as with the other above-discussed additives, humectants having active amine groups should not be used, and these include, e.g., lactamide monoethanolamine and acetamide monoethanolamine. Propylene oxide ethers of glycerin and hydrolyzed corn starch are suitable for use, but humectants based on vegetable protein are not, and these include hydrolyzed wheat protein/wheat oligosaccharides, hydrolyzed corn protein hydrolyzed wheat gluten, hyrolyzed yeast protein, hydrolyzed vegetable protein, hydrolyzed soy protein, hydrolyzed rice protein, and hydrolyzed potato protein.

Ointment Bases—include, e.g., petrolatum, polyethylene glycol, lanolin, and poloxamer, which is a block copolymer of polyoxyethylene and polyoxypropylene which may also serve as a surfactant or emulsifying agent, and which may be represented by the following structural formula:

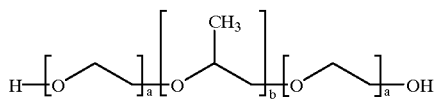

(XVI)

Penetration Enhancers—include, e.g., dimethyl isosorbide, diethyl-glycol-monoethylether, 1-dodecylazacycloheptan-2-one, and dimethylsulfoxide (DMSO).

Perfumes, Fragrances and Other Aesthetic Components—include, e.g., peppermint, rose oil, rose water, aloe vera, clove oil, menthol, camphor, eucalyptus oil, eugenol, menthyl lactate, witch hazel distillate, allantoin, bisabolol, dipotassium glycyrrhizinate, and numerous plant extracts, e.g., extract of *Matricaria chamomilla* as a counterirritant, extract of *Quillaja saponaria* Molina to provide quillaic acid, an irritant, and in the manufacture of saponin, a foaming agent, extract of *Echinacea pallida* as an immunostimulant and hyaluronidase antagonist, extract of *Hamamelis virginiana* known as witch hazel and used as an astringent, mucilaginous gel from parenchymatous tissue in leaf centers of Aloe vera Linné, useful for its emollient and wound healing activity.

Preservatives—are used to protect the pharmaceutical or cosmetological composition from degradative attack by ambient microorganisms, and include, e.g., benzalkonium chloride, benzethonium chloride, alkyl esters of p-hydroxybenzoic acid, hydantoin derivatives, cetylpyridinium chloride, monothioglycerol, phenol, phenoxyethanol, methylparagen, imidazolidinyl urea, sodium dehydroacetate, propylparaben, quaternary ammonium compounds, especially polymers such as polixetonium chloride, potassium benzoate, sodium formaldehyde sulfoxylate, sodium propionate, and thimerosal.

Sequestering Agents—comprising cyclodextrins have been used heretofore to improve the stability of dihydroxyacetone and other active agents. The cyclodextrins are a family of natural cyclic oligosaccharides capable of forming inclusion complexes with a variety of materials, and are of varying ring sizes, those having 6-, 7- and 8-glucose residues in a ring being commonly referred to as α-cyclodextrins, β-cyclodextrins, and γ-cyclodextrins, respectively. Suitable cyclodextrins include, e.g., α-cyclodextrin, β-cyclodextrin, γ-cyclodextrin, δ-cyclodextrin and cationized cyclodextrins.

Solvents—a number of which have already been discussed, include, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water.

Stabilizers—include, e.g., calcium saccharate and thymol.

Stiffening Agents—include, e.g., cetyl esters wax, myristyl alcohol, parafin, synthetic parafin, emulsifying wax, microcrystalline wax, white wax and yellow wax.

Sugars—are sometimes used with self-tanning compositions to improve the results obtained, and include, e.g., monosaccharides, disaccharides and polysaccharides such as glucose, xylose, fructose, reose, ribose, pentose, arabinose, allose, tallose, altrose, mannose, galactose, lactose, sucrose, erythrose, glyceraldehyde, or any combination thereof.

Sunscreen Agents—which are conventionally employed to block or reduce the amount of ultraviolet radiation impinging upon the skin, can also be used in combination with the self-tanning compositions of the present invention as an adjunct or as complementary thereto, allowing both a natural and artificial tan to be achieved at the same time. Typical sunscreen agents include both organic compounds and their salts as well as inorganic particulate matereials, and are generally surmised to provide protection from ultraviolet radiation by mechanism which include absorption, scattering, and reflection of the ultraviolet radiation. Any one or more of the conventional sunscreen agents well known in the art may be employed for these purposes in the compositions of the present invention and incude, e.g., 2-ethylhexyl-p-methoxycinnamate; 2-ethylhexyl-N,N-dimethyl-p-aminobenzoate; 4-N,N-(2-ethylhexyl) methylaminobenzoic acid ester with 4-(2-hydroxyethoxy) dibenzoyl-methane, p-aminobenzoic acid; 2-phenylbenzimidazole-5-sulfonic acid; octocrylene; oxybenzone; homo-menthyl salicylate; octyl salicylate; 4,4'-methoxy-t-butyldibenzoylmethane; 4-isopropyl-dibenzoylmethane; 3-benzylidene camphor; 3-(4-methylbenzylidene)camphor; titanium dioxide; zinc oxide; silica; and iron oxide.

Surfactants—are employed to provide stability to multicomponent compositions, enhance existing properties of those compositions, and bestow desirable new characteristics to said compositions. They are used as wetting agents, antifoam agents, for reducing the surface tension of water, and as emulsifiers, dispersing agents and penetrants, and include, e.g., lapyrium chloride; laureth 4, i.e., α-dodecyl-ω-hydroxy-poly(oxy-1,2-ethanediyl) or polyethylene glycol monododecyl ether; laureth 9, i.e., a mixture of polyethylene glycol monododecyl ethers averaging about 9 ethylene oxide groups per molecule; monoethanolamine; nonoxynol 4, 9 and 10, i.e., polyethylene glycol mono(p-nonylphenyl) ether; nonoxynol 15, i.e., α-(p-nonylphenyl)-ω-hydroxypentadeca(oxyethylene); nonoxynol 30, i.e., α-(p-nonylphenyl)-ω-hydroxytriaconta(oxyethylene); poloxalene, i.e., nonionic polymer of the polyethylene-polypropylene glycol type, MW=approx. 3000; poloxamer (see ointment bases above); polyoxyl 8, 40 and 50 stearate, i.e., poly(oxy-1,2-ethanediyl), α-hydro-ω-hydroxy-, octadecanoate; polyoxyl 10 oleyl ether, i.e., poly(oxy-1,2-ethanediyl), α-[(Z)-9-octadecenyl-ω-hydroxy-; polysorbate 20, i.e., sorbitan, monododecanoate, poly(oxy-1,2-ethanediyl); polysorbate 40, i.e., sorbitan, monohexadecanoate, poly(oxy-1,2-ethanediyl); polysorbate 60, i.e., sorbitan, monooctadecanoate, poly(oxy-1,2-ethanediyl); polysorbate 65, i.e., sorbitan, trioctadecanoate, poly(oxy-1,2-ethanediyl); polysorbate 80, i.e., sorbitan, mono-9-monodecenoate, poly(oxy-1,2-ethanediyl); polysorbate 85, i.e., sorbitan, tri-9-octadecenoate, poly(oxy-1,2-ethanediyl); sodium lauryl sulfate; sorbitan monolaurate; sorbitan monooleate; sorbitan monopalmitate; sorbitan monostearate; sorbitan sesquioleate; sorbitan trioleate; and sorbitan tristearate. A further description of additional types of auxiliary ingredients which may optionally be included in the compositions of the present invention, as well as of specific compositions of those types and of the above-described types which may thus be optionally included, may be found in the CTFA International Cosmetic Ingredient Dictionary 4th ed., The Cosmetic, Toiletry, and Fragrance Association, Inc., Washington, D.C., 1991.

Lubricity, which refers to the property of having a smooth or slippery quality, is a desirable property of the compositions of the present invention that can be enhanced by the addtion of agents well known in the art for this purpose. In particular, a silicone oil or fluid is preferably used since it can provide the desired lubricity and emollience without a greasy feel. Examples of such agents include dimethyl polysiloxane and methylphenyl polysiloxane which are water-soluble, and silicone glycol copolymer which is alcohol-soluble. Polysiloxanes which are commonly employed include dimethyl polysiloxane which is end-blocked with trimethyl units, the CTFA name for which is dimethicone, and polydimethylcyclosiloxane, the CTFA name for which is cyclomethicone. Such preferred siloxanes exhibit a viscosity of from about 2 to about 50 centistokes at 25° C. and are employed in sufficient amount to aid in stimulating removal of dry scale from the skin and to aid in controlling conditioning of the skin, which will usually be from about 0.1% to about 10.0% by weight, based on the total weight of the composition, and preferably will be from about 1.0% to about 3.0% by weight.

The cosmetologically acceptable carrier employed in the compositions of the present invention may be an emulsion which is a silicone-in-water emulsion. Water-in-oil emulsions can also be utilized to prepare lotions and creams, and oil in that event will be the continuous phase, and the ratio of the amounts of oil to water will be in the range of from about 2:1 to about 1:100, and preferably will be from about 1:1 to about 1:10. A silicone-in-water emulsion is typically comprised of a mixture of hydrocarbons and silicones in water, e.g., a mixture of hydrocarbons, volatile silicones, and alkylated derivatives of polymeric silicones such as hyrogenated polyisobutene, cyclomethicone, and cetyl dimethicone. The term "volatile" as applied to silicone oils, refers to those materials which have a measurable vapor pressure at ambient temperatures. Volatile silicone oils are preferably chosen from cyclic or linear polydimethylsiloxanes containing from about 3 to about 9, and preferably from about 4 to about 5, silicon atoms. The nonvolatile silicone oils which are useful in preparing the compositions of the present invention are, e.g., polyalkyl siloxanes, polyalkylaryl siloxanes, and polyether siloxane copolymers. Useful polyether siloxane copolymers include a polyoxyalkylene ether copolymer having a viscosity of about 1200 to 1500 centistokes at 25° C., available as SF-1066 organosilicone surfactant from General Electric. Cetyl dimethicone copolyol and cetyl dimethicone are especially useful because they also function as emulsifiers and emollients. In such compositions, as well as in other compositions of the present invention, it has been found that sodium chloride is a useful stabilizing agent.

Indeed, the overall viscosity of the compositions of the present invention may exhibit considerable variation, some of which is by design and is a product of the type of formulation which is being prepared. For example, a cream formulation will inherently have a higher viscosity than an aerosol spray formulation. Generally, however, with the two key properties of stability and dispersibility being of paramount interest, the viscosity of the compositions of the present invention will desirably between about 2000 and about 20,000 cps. When the viscosity is below about 2000 cps., the compositions will exhibit a reduced stability; whereas, when the viscosity is above about 20,000 cps., it will be difficult to disperse the compositions of the present invention by ordinary means.

The compositions of the present invention may be prepared using very straightforward methodology which is well understood by the artisan of ordinary skill. Where the compositions of the present invention are simple aqueous and/or other solvent solutions, the various components of the overall composition are brought together in any practical order, which will be dictated largely by considerations of convenience. Those components having reduced water solubility, but sufficient solubility in the same co-solvent with water, may all be a dissolved in said co-solvent, after which the co-solvent solution will be added to the water portion of the carrier whereupon the solutes therein will become dissolved in the water. To aid in this dispersion/solution process, a surfactant may be employed.

Where the compositions of the present invention are to be in the form of emulsions, as where the resultant formulation is a lotion or a cream, the components of the composition will be brought together in accordance with the following general procedures. The continuous water phase is first heated to a temperature in the range of from about 600 to about 95° C., preferably from about 70° to about 85° C., and more preferably from about 75° to about 80° C., the choice of which temperature will depend, of course, upon the physical and chemical properties of the components which make up the oil-in-water emulsion. Once the continuous water phase has reached its selected temperature, the components of the final composition which are to be added at this stage, referred to as Phase I, are admixed with the water and dispersed therein under high-speed agitation. Next, the temperature of the water is restored to appoximately its original level, after which the Phase II components of the composition are added to the composition mixture under moderate agitation and mixing continues for from about 5 to about 60 minutes, preferably about 10 to about 30 minutes, depending on the components of Phases I and II. Thereafter, the composition mixture is passively or actively cooled to from about 20° to about 55° C., preferably to from about 350 to about 45° C., after which the components of the remaining Phases III, IV and V are combined and added to the composition mixture. The composition mixture is then actively or passively cooled to from about 20° to about 40° C., preferably to about 30° C., after which the fragrance phase is added to the composition mixture, to which water is then added in sufficient quantity to reach its original predetermined concentration in the overall composition.

In accordance with the present invention it has been discovered that substantially improved chemical, including pH stability can be conferred upon aqueous formulations containing self-tanning skin coloring agents subject to such instability, especially where the self-tanning agent is an α-hydroxy aldehyde or ketone, more especially 1,3-dihydroxyacetone. The basic mechanisms whereby such self-tanning agents are stabilized in accordance with the present invention are contemplated to be applicable across a broad range of such self-tanning agents. Accordingly, the discussion which follows, relating to such mechanisms of action which are hypothesized to take place with regard to the stabilization of aqueous formulations containing 1,3-dihydroxyacetone, will be understood to be merely demonstrative of the present invention, and therefore to be applicable to many other self-tanning agents within the scope of the present invention.

The compositions of the present invention utilize water-soluble alcohols ("-ols"), alkoxylated -ols and dihydric alcohols ("-diols") together to provide chemical and pH stability for up to 8 hours at 80° C., which is comparatively much superior to the results obtained with aqueous formulations which do not contain these components. It is theorized that the keto functionality of 1,3-dihydroxyacetone is capable of undergoing ketal formation, analogous to acetal formation, in the presence of 1,2-diols and $H_3O^+$, and that the use of 1,2-diols or polyols containing vicinal hydroxyl functions, at a 1:1 molar ratio, is required for this chemical pathway to operate efficiently. It is conjectured that the presence of $H_3O^+$ in this system shifts the equilibrium of the reaction in this pathway from a keto-containing moiety to a five-membered cyclic ketal structure which is more stable than the monomeric 1,3-dihydroxyacetone form and thus more resistant to degradation. This theorized pathway may be represented by the following reaction:

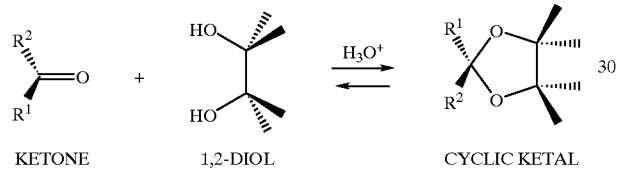

It is thought that within a pH range of from 3.5 to 4.5 and at ambient temperatures, 1,3-dihydroxyacetone is in equilibrium with this supposed cyclic ketal structure in the above-mentioned reaction and thereby stabilized. When an aqueous formulation within the scope of the present invention is applied to the skin, the pH of the system is elevated to 5.5 which substantially reverses said reaction, i.e., halts cyclic ketal formation. There is produced on the skin as a consequence the otherwise unstable monomeric form, 1,3-dihydroxyacetone, which must be present in order for the Maillard reaction with the skin to take place, which results in the desired artificial tanning. It may be seen, accordingly, that the present invention provides a means for stabilizing 1,3-dihydroxyacetone for long periods of time by converting it to a cyclic ketal while it is being stored as an aqueous formulation ready for use. The cyclic ketal is stable but incapable of producing the self-tanning reaction on the skin. Surprisingly, this same stabilized aqueous formulation of the present invention, when applied to the skin, permits reversion of the cyclic ketal back to the unstable 1,3-dihydroxyacetone, which rapidly produces the self-tanning reaction, making its instability of no consequence.

It is further theorized that the keto functionality of 1,3-dihydroxyacetone undergoes cyclic ketal formation in the presence of polyols ("-ols") and $H_3O^+$ and that the use of such a water soluble alcohol in a 2:1 molar ratio is required for this pathway to operate efficiently. Although 1,3-dihydroxyacetone reduces the pH of an aqueous solution to which it is added, the presence of $H_3O^+$ produces stability in this system by shifting the equilibrium of the reaction in this pathway from a keto-containing moiety to a more stable five-membered cyclic ketal structure, as already above-described. This pathway may be represented by the following scheme:

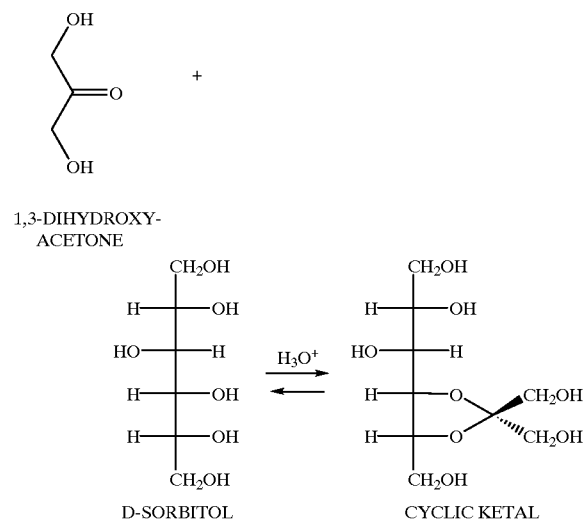

With some polyols, it is possible to form more than one cyclic ketal with the polyol, as is the case with mannitol, as illustrated in the following reaction scheme:

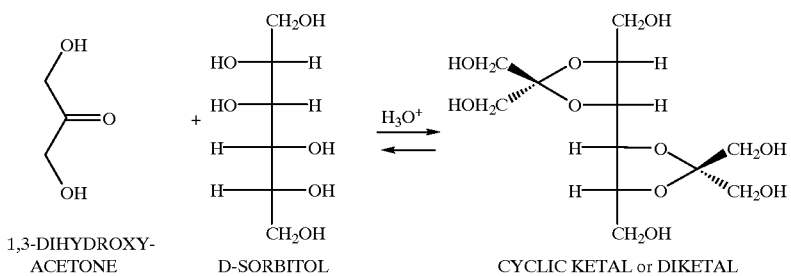

An alcohol which has demonstrated good synergy with 1,3-dihydroxyacetone is benzyl alcohol. Although benzyl alcohol is commonly used as a preservative in cosmetologic products, it is theorized that this aromatic alcohol reacts with 1,3-dihydroxyacetone to form a more stable cyclic ketal in much the same manner as above-described with respect to short chain primary alcohols, but at a much slower rate of reaction. The phenyl functionality of benzyl alcohol confers upon it a degree of hydrophobicity which makes it impracticable to use 2:1 molar ratios of the benzyl alcohol, its solubility in water being exceeded at these levels.

It is further theorized that hydrogen bonding plays an important role in the stabilization of 1,3-dihydroxyacetone in accordance with the present invention. In aqueous solution, 1,3-dihydroxyacetone is converted from a dimeric to a monomeric form, only the latter being active as a self-tanning agent. Hydrogen bonding plays a role in maintaining 1,3-dihydroxyacetone in the monomeric form, and if sufficient portion of the aqueous solvent are bound by other excipients, or are lost by evaporation, the amount of possible hydrogen bonding is reduced.

It is thought that the -ols, -diols, and alkoxylated ethers present in the compositions of the present invention aid in providing sufficient hydrogen bonding at the hydroxyl functionalities of 1,3-dihydroxyacetone well solvated and thus in the desired monomeric form. Alkoxylated ethers, especially diethylene glycol monoethyl ether, i.e., ethoxydiglycol, exhibit acidity in aqueous solution which will be favorable to the conditions necessary for optimal 1,3-dihydroxyacetone stability. Ethoxydiglycol, present in the amounts preferred for the compositions of the present invention, will result in a pH of said composition of about 4.7, prior to addition of the 1,3-dihydroxyacetone. This factor, in addition to the three site available for hydrogen bonding, makes ethoxydiglycol a preferred component for the compositions of the present invention.

DESCRIPTION OF PREFERRED EMBODIMENTS

There follows a description of certain preferred embodiments of the compositions of the present invention, as well as a description of the methodology employed to evaluate the improved stability and other enhanced properties of said compositions, including the results of those evaluations. However, the following description is presented solely for the purpose of further illustrating the invention and is in no way intended to be, nor should it be construed to be a limitation of any sort on the scope or any of the essential or auxiliary features of the present invention, which are to be determined and defined solely by the attendant claims which form a part hereof.

EXAMPLE 1

Self-Tanning Cosmetic Formulation in Spray Form for Producing a Dark Tan

The individual components of the spray formulation, identified in Table 1 below, were brought together in four phases, i.e., four different groups of components were added separately to the vessel in which the formulation was being prepared largely as a matter of convenience. As a practical matter, all of the components of the formulation were brought into admixture with each other in a single step, and the order of addition was not critical, but was, rather, also a matter of convenience.

TABLE 1

| PHASE NO. | INGREDIENT DESCRIPTION | GRADE | % BY WT. PER TOTAL WT. OF COMP. |
|---|---|---|---|
| I | Deionized Water | — | 70.75 |
| I | Edetate Disodium | USP[1] | 0.10 |
| I | Ethoxydiglycol | — | 20.00 |
| I | Benzyl Alcohol (and) Methyl-paraben (and) Propylparaben | — | 0.35 |
| I | Sorbitol Solution | USP | 1.00 |
| I | Dihydroxyacetone | — | 4.00 |
| II | Nonoxynol-9 | — | 0.50 |
| II | Fragrance | — | 0.10 |
| III | Panthenol | — | 0.20 |
| III | Retinyl Palmitate, Water Miscible | — | 0.20 |
| III | Propylene Glycol (and) Walnut Extract | — | 1.00 |
| III | Butylene Glycol (and) Water (and) Aloe Extract (and) Matricaria Extract (and) Coneflower Extract (and) Quillaja Saponaria Extract (and) Witch Hazel Extract | — | 1.50 |
| III | Propylene Glycol (and) Water (and) Kiwi Fruit Extract | — | 0.20 |
| IV | Sorbic Acid | NF[2] | 0.05 |
| IV | Sodium Benzoate | NF | 0.05 |

EXAMPLE 2

Self-Tanning Cosmetic Formulation in Spray Form for Producing a Deep Dark Tan

The individual components of the spray formulation, identified in Table 2 below, were brought together in essentially the same manner as above-described in Example 1. Four phases of components were added separately to the vessel largely as a matter of convenience. The darker tan produced by the formulation of this example, compared to that produced by the formulation of Example 1 above, is the result of 50% more of the active self-tanning agent, dihydroxyacetone, present in this example.

TABLE 2

| PHASE NO. | INGREDIENT DESCRIPTION | GRADE | % BY WT. PER TOTAL WT. OF COMP. |
|---|---|---|---|
| I | Deionized Water | — | 68.75 |
| I | Edetate Disodium | USP | 0.10 |
| I | Ethoxydiglycol | — | 20.00 |
| I | Benzyl Alcohol (and) Methylparaben (and) Propylparaben | — | 0.35 |
| I | Sorbitol Solution | USP | 1.00 |
| I | Dihydroxyacetone | — | 6.00 |
| II | Nonoxynol-9 | — | 0.50 |
| II | Fragrance | — | 0.10 |
| III | Panthenol | — | 0.20 |
| III | Retinyl Palmitate, Water Miscible | — | 0.20 |
| III | Propylene Glycol (and) Walnut Extract | — | 1.00 |
| III | Butylene Glycol (and) Water (and) Aloe Extract (and) Matricaria Extract (and) Coneflower Extract (and) *Quillaja Saponaria* Extract (and) Witch Hazel Extract | — | 1.50 |
| III | Propylene Glycol (and) Water (and) Kiwi Fruit Extract | — | 0.20 |
| IV | Sorbic Acid | NF | 0.05 |
| IV | Sodium Benzoate | NF | 0.05 |

EXAMPLE 3

Self-Tanning Cosmetic Formulation in Oil-in-Water Emulsion Cream Form for Producing a Deep Dark Tan The continuous water phase was first heated to a temperature of 75° to 80° C., after which the components of Phase I set out in Table 3 below, were admixed with the water and dispersed therein under high-speed agitation. Next, the temperature of the water was restored to 75° C., after which the Phase II components set out in Table 3 were added to the composition mixture under moderate agitation, and mixing continued for 10 to 30 minutes. Thereafter, the composition mixture was actively cooled to 35° to 45° C., after which the components of the remaining Phases III, IV and V set out in Table 3 were combined and added to the composition mixture. The composition mixture was then actively cooled to 30° C., after which the fragrance phase was added to the composition mixture, to which water was then added in sufficient quantity to reach the concentration set out in Table 3.

TABLE 3

| PHASE NO. | INGREDIENT DESCRIPTION | GRADE | % BY WT. PER TOTAL WT. OF COMP. |
|---|---|---|---|
| I | Purified Water | USP | 67.800 |
| I | Xanthan Gum | NF | 0.350 |
| I | Ethoxydiglycol | — | 5.000 |
| I | $C_{10}$–$C_{30}$ acrylate cross polymers[3] | — | 0.100 |
| I | Sorbitol 70% By Weight Solution | NC[4] | 5.000 |
| I | Diethanolamine cetyl phosphate | — | 0.100 |
| II | Cetyl Alcohol | NF | 1.500 |
| II | Stearyl Alcohol | — | 1.500 |
| II | Steareth-20 | — | 1.000 |
| II | Octyl Palmitate | — | 1.500 |
| II | Dimethicone Copolyol[5] | — | 1.000 |
| II | Glyceryl Stearate (and) PEG-100[6] Stearate[7] | — | 0.500 |
| II | α-Tocopherol Acetate (Vitamin E) | — | 0.100 |
| II | Dimethicone 350[8] | — | 0.050 |
| II | Actiplex 335 Lipo M | — | 0.100 |
| II | Glucan P-20 Distearate[9] | — | 1.500 |
| II | Dihydroxyacetone | — | 5.000 |
| III | Plant Extracts[10] | — | 0.250 |
| IV | Sodium meta-Bisulfite | — | 0.025 |
| IV | Purified Water | USP | 6.150 |
| IV | 50% Aqueous DL-Panthenol | — | 0.400 |

TABLE 3-continued

| PHASE NO. | INGREDIENT DESCRIPTION | GRADE | % BY WT. PER TOTAL WT. OF COMP. |
|---|---|---|---|
| V | Stearyl Glycerrhetinate | — | 0.025 |
| Va | Fragrance | — | 0.100 |

[3] Available from B. F. Goodrich under the trademark Pemulen TR-1.
[4] Non-crystallized = USP grade.
[5] Available from Goldschmidt under the trademark Abil Wax 9001.
[6] Polyethylene glycol, approx. mol. wt. of 100.
[7] Available from_____under the trademark Arlacel 165.
[8] 350 centistokes (cst).
[9] Polypropylene-20/glucan distearate ether.
[10] Extracts of exotic plants available from Nipa under the trademark Nipaguard MPA.

EXAMPLE 4

Evaluation of Stability of Dihydroxyacetone in a Composition of the Present Invention When Subjected to Harsh Storage Conditions In order to evaluate the extent to which a typical composition of the present invention was able to protect the dihydroxyacetone (DHA) contained in said composition from degradation under harsh storage conditions, the composition set out in Table 5 below was stored at 25° C. for three (3) months and at 50° C. for two (2) months. The pH of each composition and the dihydroxyacetone content of each were measured at the beginning of the storage period and at the conclusion of the storage period. The results obtained are illustrated in the following table of values designated as Table 4.

TABLE 4

| COMPOSITION STORAGE CONDITIONS | BEGINNING pH | FINAL pH | BEGINNING DHA CONC. (wt. %) | FINAL DHA CONC. (wt. %) |
|---|---|---|---|---|
| 3 mos. at 25° C. | 4.7 | 4.3 | | |
| 2 mos. at 50° C. | 4.7 | 4.0 | 6.0 | 5.2 |

What is claimed is:

1. A composition comprising:
   (A) from about 0.5% to about 20% by weight, based on the total weight of said composition, of a self-tanning skin coloring agent subject to chemical instability;
   (B) from about 2% to about 40% by weight, based on the total weight of said composition, of a polyethoxyglycol having the formula

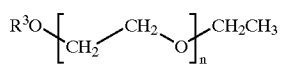

wherein n is an integer of from 2 to 6 and $R^3$ is H, ($C_1$ to $C_6$) alkyl or phenyl;

TABLE 5

| PHASE NO. | INGREDIENT DESCRIPTION | GRADE | % BY WT. PER TOTAL WT. OF COMP. |
|---|---|---|---|
| I | Purified Water | USP | 68.75 |
| I | Edetate Disodium | USP | 0.10 |
| I | Trivalin SF | — | 20.00 |
| I | Plant Extracts[11] | — | 0.35 |
| I | Sorbitol Solution | USP | 1.00 |
| I | Dihydroxyacetone | — | 6.00 |
| II | Nonoxynol-9 | — | 0.50 |
| II | Fragrance | — | 0.10 |
| III | dL-Panthenol | — | 0.20 |
| III | Retinyl Palmitate, Water Miscible | — | 0.20 |
| III | Propylene Glycol (and) Walnut Extract | — | 1.00 |
| III | Butylene Glycol (and) Water (and) Aloe Extract (and) Matricaria Extract (and) Coneflower Extract (and) *Quillaja Saponaria* Extract (and) Witch Hazel Extract | — | 1.50 |
| III | Propylene Glycol (and) Water (and) Kiwi Fruit Extract | — | 0.20 |
| IV | Sorbic Acid | NF | 0.05 |
| IV | Sodium Benzoate | NF | 0.05 |

[11] Extracts of exotic plants available from Nipa under the trademark Nipaguard MPA.

(C) from about 0.1% to about 15% by weight, based on total weight of said composition, of a polyol selected from the group consisting of 1,2,6-hexanetriol, isopropylidene glycerol, polyoxyethylene sorbitols, glycerin, diglycerin, erythritol, mannitol, xylitol, D- and L-sorbitol, glucose, fructose, galactose, mannose, sucrose, lactose, trehalose, maltose and inositol;

(D) from about 0.1 to about 8% by weight, based on total weight of said composition, of a water soluble dihydroxyl compound selected from the group consisting of ethylene glycol, diethylene glycol, triethylene glycol, water-soluble polyethylene glycols, 1,2-propanediol, 1,3-propanediol, 2-methyl-1,3-propanediol, dipropylene glycol, water-soluble propylene glycols, 1,2-butanediol, 1,3-butanediol, 1,4-butanediol, pentanediols, 1,6-hexanediol, 2-ethyl-1,3-hexanediol and mixtures of any two or more thereof; and (E) an acidifying agent in an amount sufficient to maintain pH of the composition at about 3.5 to about 4.5.

2. A composition comprising:

(A) from about 0.5% to about 20.0% by weight, based on total weight of said composition, of a self-tanning skin coloring agent subject to chemical instability;

(B) from about 2.0% to about 40.0% by weight, based on total weight of said composition of a polyethoxyglycol;

(C) from about 0.1% to about 15.0% by weight, based on total weight of said composition, of a polyol comprising a polyhydric compound having at least three hydroxyl groups and at least three carbon atoms;

(D) from about 0.1% to about 8.0% by weight, based on total weight of said composition of a water soluble dihydroxyl compound having at least two, and up to eight carbon atoms; and (E) an acidifying agent in an amount sufficient to maintain the pH of said total composition at from about 3.5 to about 4.5.

3. The composition according to claim 2 wherein said acidifying agent is one or more members selected from the group consisting essentially of acetic, adipic, anisic, benzoic, boric, carbonic, cinnamic, citric, diphosphonic, formic, fumaric gallic, glutaric, glycolic, lactic, maleic, malic, malonic, oxalic, phthalic, propionic, pyrogallic, pyruvic, salicylic, succinic, tartaric, and vanillic acid.

4. The composition according to claim 2 wherein said acidifying agent is one or more members selected from the group consisting essentially of sorbic acid, acetic acid, maleic acid, citric acid and fumaric acid.

5. The composition according to claim 1 wherein the self-tanning skin coloring agent comprises dihydroxyacetone.

6. The composition according to claim 1 wherein the polyethoxyglycol comprises ethoxydiglycol.

7. The cosmetologic product for application to the hair, nails or skin of a subject for the purpose of tanning, coloring and/or darkening the same, comprising a composition according to claim 1 wherein a remaining weight percent portion of said composition comprises a cosmetologically acceptable carrier.

8. The cosmetologic product according to claim 7 wherein said cosmetologically acceptable carrier comprises one or more members independently selected from the group consisting of acidifying and alkalizing agents; aerosol propellants; antimicrobial agents; antimicrobial preservatives; antioxidants; buffering agents; chelating agents; coloring additives; dermatologically active agents; dispersing agents; emollients; emulsifying agents; excipients; humectants; ointment bases; penetration enhancers; perfumes and fragrances; preservatives; sequestering agents; solvents; stabilizers; stiffening agents; sugars; sunscreen agents; surfactants; suspending agents; thickening agents; vehicles; viscosity-increasing agents; wetting agents; and wetting and/or solubilizing agents.

9. The method of tanning, coloring or darkening the hair, nails and/or skin of a subject comprising applying thereto an amount of cosmetologic product according to claim 7 sufficient to tan, color, or darken said hair, nails and/or skin of said subject to which it is applied to the extent desired by said subject.

10. The method for preparing a cosmetologic product according to claim 7 wherein said product is an aqueous solution, comprising the following steps, carried out sequentially or simultaneously:

(1) combining the following components of said product: water, a self-tanning skin coloring agent, a polyethoxyglycol and a polyol, optionally together with chelating agents, sequestering agents, antimicrobial preservatives, and/or antioxidants which are desired, and optionally with a solvent therefor; and thereafter optionally:

(2) adding a perfume or fragrance which is desired optionally with a solvent therefor;

(3) adding vitamins, nutrients, penetration enhancing agents, coloring additives, sunscreen agents, and/or dermatologically active agents which are desired, optionally with a solvent therefor; and (4) adding antimicrobial preservatives which are desired, optionally with a solvent therefor.

11. A composition comprising:

(A) from about 4% to about 6% by weight, based on the total weight of said composition, of dihydroxyacetone;

(B) from about 14% to about 25% by weight, based on the total weight of said composition, of ethoxydiglycol;

(C) from about 0.5% to about 1.5% by weight, based on the total weight of said composition, of D-sorbitol;

(D) from about 0.4% to about 2% by weight, based on the total weight of said composition, of propylene glycol, butylene glycol or mixtures thereof; and (E) from about 0.04% to about 0.2% by weight, based on the total weight of the composition, of sorbic acid.

12. The cosmetologic product for application to the hair, nails or skin of a subject for the purpose of tanning, coloring and/or darkening the same, comprising a composition according to claim 11 wherein a remaining weight percent portion of said composition comprises a cosmetologically acceptable carrier.

13. The cosmetologic product according to claim 12 wherein said cosmetologically acceptable carrier comprises one or more members independently selected from the group consisting of acidifying and alkalizing agents; aerosol propellants; antimicrobial agents; antimicrobial preservatives; antioxidants; buffering agents; chelating agents; coloring additives; dermatologically active agents; dispersing agents; emollients; emulsifying agents; excipients; humectants; ointment bases; penetration enhancers; perfumes and fragrances; preservatives; sequestering agents; solvents; stabilizers; stiffening agents; sugars; sunscreen agents; surfactants; suspending agents; thickening agents; vehicles; viscosity-increasing agents; wetting agents; and wetting and/or solubilizing agents.

14. The composition of claim 1, wherein the self-tanning skin coloring agent comprises an α-hydroxy aldehyde or ketone having the formula:

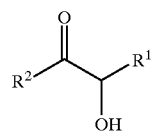

in which $R^1$ is H, $CH_2OH$, $CH(OH)CH_2OH$, $CH(OH)CH(O)$, $CH(OCH_3)CH(O)$, $CH(NH_2)CH(O)$, or $CH(NHC_6H_5)CH(O)$ and $R^2$ is H or $CH_2OH$.

15. The composition of claim 1, wherein the self-tanning skin coloring agent comprises dihydroxyacetone.

16. The composition of claim 1, wherein the self-tanning skin coloring agent is present in amounts about 2 to about 10 percent by weight.

17. The composition of claim 1, wherein the polyethoxyglycol comprises ethoxydiglycol.

18. The composition of claim 1, wherein the polyol comprises one or more members selected from the group consisting of sorbitol, mannitol and inositol.

* * * * *